US012697314B2

(12) United States Patent
Osafune et al.

(10) Patent No.: US 12,697,314 B2
(45) Date of Patent: *Aug. 4, 2026**

(54) PHARMACEUTICAL COMPOSITION FOR TREATING AUTOSOMAL DOMINANT POLYCYSTIC KIDNEY DISEASE

(71) Applicants: Kyoto University, Kyoto (JP); National University Corporation Hokkaido University, Hokkaido (JP)

(72) Inventors: Kenji Osafune, Kyoto (JP); Shinichi Mae, Kyoto (JP); Saori Nishio, Sapporo (JP); Fumihiko Hattanda, Sapporo (JP); Tsuyoshi Nakano, Kyoto (JP); Ryuichiro Hirayama, Kyoto (JP); Tomoko Suzuki, Kyoto (JP); Ayuto Hayashi, Kyoto (JP)

(73) Assignees: KYOTO UNIVERSITY, Kyoto (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/242,517

(22) Filed: Jun. 18, 2025

(65) Prior Publication Data

US 2026/0124164 A1     May 7, 2026

Related U.S. Application Data

(63) Continuation of application No. PCT/JP2024/046002, filed on Dec. 25, 2024.

(30) Foreign Application Priority Data

Nov. 6, 2024     (JP) ................................. 2024-194582

(51) Int. Cl.
A61K 31/192     (2006.01)
A61P 13/12     (2006.01)

(52) U.S. Cl.
CPC ............ *A61K 31/192* (2013.01); *A61P 13/12* (2018.01)

(58) Field of Classification Search
CPC ............................. A61K 31/192; A61P 13/12
See application file for complete search history.

(56) References Cited

U.S. PATENT DOCUMENTS

2016/0355888 A1* 12/2016 Chen ....................... A61P 15/14
2020/0248148 A1   8/2020 Sueta et al.
2024/0010989 A1   1/2024 Osafune et al.
2025/0170083 A1   5/2025 Osafune et al.

FOREIGN PATENT DOCUMENTS

WO        2018/216743        11/2018
WO        2021/075585        4/2021
WO        2022/149616        7/2022
WO        2022/210968        10/2022
WO        2024/090521        5/2024

OTHER PUBLICATIONS

Nair et al. Journal of Basic and Clinical Pharmacy 2016, 7 (2), 27-31.*
Co-pending U.S. Appl. No. 19/041,480, effective filing date Jan. 30, 2025.*
Vicente E. Torres et al., "Tolvaptan in Patients with Autosomal Dominant Polycystic Kidney Disease", The New England Journal of Medicine, 367, Dec. 2012, pp. 2407-2418.
Shin-Ichi Mae et al., "Expansion of Human iPSC-Derived Ureteric Bud Organoids with Repeated Branching Potential", Cell Reports, 32, 107963, 2020, pp. 1-16.
Tsukasa Nakamura et al., "Elevation of Serum Levels of Metalloproteinase-1, Tissue Inhibitor of Metalloproteinase-1 and Type IV Collagen, and Plasma Levels of Metalloproteinase-9 in Polycystic Kidney Disease", Am J Nephrol, 20, 2000, pp. 32-36.
Tomonaga Ameku et al., "Identification of MMP1 as a novel risk factor for intracranial aneurysms in ADPKD using iPSC models", Scientific Reports, 6:30013, Jul. 2016, pp. 1-14.
Isaline Rowe et al., "Defective glucose metabolism in polycystic kidney disease identifies a new therapeutic strategy", Nature Medicine, vol. 19, No. 4, Mar. 2013, pp. 488-493.
Kazushige Hanaoka et al., "cAMP Regulates Cell Proliferation and Cyst Formation in Autosomal Polycystic Kidney Disease Cells", J Am Soc Nephrol, 11, 2000, pp. 1179-1187.
Iram Zafar et al., "Effect of statin and angiotensin-converting enzyme inhibition on structural and hemodynamic alterations in autosomal dominant polycystic kidney disease model", Am J Physiol Renal Physiol, 293, Jun. 2007, pgs. F854-F859.

(Continued)

*Primary Examiner* — Irina Neagu
(74) *Attorney, Agent, or Firm* — Wenderoth, Lind & Ponack, L.L.P.

(57) ABSTRACT

A new dosage regimen of a pharmaceutical composition comprising tamibarotene as the active ingredient for treating autosomal dominant polycystic kidney disease. A pharmaceutical composition comprising tamibarotene for the treatment or prevention of autosomal dominant polycystic kidney disease (ADPKD), wherein the composition is administered orally to a patient with ADPKD in an amount of 1.4-5.5 mg/day, particularly 4.0 mg/day of tamibarotene.

2 Claims, 8 Drawing Sheets

(56) References Cited

OTHER PUBLICATIONS

Melissa A. Cadnapaphornchai et al., "Effect of Pravastatin on Total Kidney Volume, Left Ventricular Mass Index, and Microalbuminuria in Pediatric Autosomal Dominant Polycystic Kidney Disease", Clin J Am Soc Nephrol, May 9, 2014, pp. 889-896.

International Search Report issued Jan. 9, 2024 in International Application No. PCT/JP2023/038716, pp. 1-4.

Nguyen et al., "Synergistic Antiproliferative Effects of All-Trans Retinoic Acid and Paclitaxel on Autosomal Dominant Polycystic Kidney Disease Epithelial Cells", BioMed Research International, vol. 2021, Article ID 1242916, Oct. 2021, pp. 1-12.

Altieri et al., "N-(4-Hydroxyphenyl) Retinamide Inhibits Cystogenesis By Polycystic Epithelial Cell Lines In Vitro", Life Sciences, vol. 64, Issue 22, 1999, pp. PL259-PL265.

Papadimitriou et al., "Collecting duct cells show differential retinoic acid responses to acute versus chronic kidney injury stimuli", Scientific Reports, vol. 10, Article No. 16683, 2020, pp. 1-12.

Islam et al., "Retinoic acid-dependent activation of the polycystic kidney disease-1 (PKD1) promoter", American Journal of Physiology-Renal Physiology, vol. 295, Issue 6, 2008, pp. F1845-F1854.

Mae et al., "Human iPSC-derived renal collecting duct organoid model cystogenesis in ADPKD", Cell Reports, 42, 113431, 2023, pp. 1-24.

Caroline Thivierge et al., "Overexpression of PKD1 Causes Polycystic Kidney Disease", Molecular and Cellular Biology, vol. 26, No. 4, Feb. 2006, pp. 1538-1548.

CRL-2830™ Product Sheet, WT 9-7, ATCC, Feb. 8, 2024, pp. 1-7.

Olivier Devuyst et al., "Expression of aquaporins-1 and -2 during nephrogenesis and in autosomal dominant polycystic kidney disease", Am. J. Physiol., 271 (1Pt2), Jul. 1996, pp. F169-F183.

Samsca® package insert (with partial English translation), 2022, pp. 1-3.

Byungdo B. Han et al., "Fenretinide perturbs Focal Adhesion Kinase in Premalignant and Malignant Human Oral Keratinocytes. *Fenretinide's chemopreventive mechanisms include ECM interactions*", Cancer Prev Res (Phila), 8(5), May 2015, pp. 419-430.

Jinzhao He et al., "Inhibiting Focal Adhesion Kinase Ameliorates Cyst Development in Polycystin-1-Deficient Polycystic Kidney Disease in Animal Model", JASN, 32, 2021, pp. 2159-2174.

Carsten Bergmann et al., "Polycystic kidney disease", Nature Reviews, Disease Primers, Article citation ID: (2018) 4:50, 2018, pp. 1-24.

Tracy Tran et al., "A scalable organoid model of human autosomal dominant polycystic kidney disease for disease mechanism and drug discovery", Cell Stem Cell, 29, 2022, pp. 1083-1101.

Lixi Li et al., "Tamibarotene inhibit the accumulation of fibrocyte and alleviate renal fibrosis by IL-17A", Renal Failure, 2020, vol. 42, No. 1, pp. 1173-1183.

"Medical Drugs: Amnolake", Amnolake® Tablet 2 mg Package Insert, Oct. 2022 Revision, 1st Edition, with English language translation, pp. 1-12.

"Phase II clinical trial begins for polycystic kidney disease drug candidate identified by iPS cell-based drug discovery", https://www.regenephro.co.jp/news/2024-02-29/ and https://www.regenephro.co.jp/en/news/2024-02-29, (2024), pp. 1-25.

"Phase II Clinical Trial Begins for Autosomal Dominant Polycystic Kidney Disease Drug Candidate Identified by iPS Cell-based Drug Discovery", Center for iPS Cell Research and Application, Kyoto University, Feb. 29, 2024, pp. 1-7, https://www.cira.kyotou.ac.jp/j/pressrelease/news/240229-150000.html and https://www.cira.kyotou.ac.jp/e/pressrelease/news/240229-150000.html.

Study Details, Study of Tamibarotene in Patients with ADPKD, National Library of Medicine, National Center for Biotechnology Information, Mar. 4, 2024, https://clinicaltrials.gov/study/NCT06289998, pp. 1-8.

Study of Tamibarotene in Patients With ADPKD, Study Record Version 1: NCT06289998, ClinicalTrials.gov archive, Feb. 25, 2024, pp. 1-9.

Shinichi Mae et al., "Japanese Journal of Nephrology", 66th Annual Meeting of Japanese Society of Nephrology, vol. 65, No. 3 (113-376), 2023, pp. 1-4, with English translation.

Non-Final Office Action issued May 5, 2025 in U.S. Appl. No. 19/041,480, pp. 1-8.

International Preliminary Report on Patentability issued Apr. 29, 2025 in International Application No. PCT/JP2023/038716, pp. 1-7.

Extended European Search Report issued Nov. 26, 2025 in related European Patent Application No. 23882723.2.

Marijn F. Stockman et al., "Renal Ciliopathies: Sorting Out Therapeutic Approaches for Nephronophthisis", Frontiers in Cell and Developmental Biology, vol. 9, Article 653138, pp. 1-30, May 13, 2021.

* cited by examiner

Figure 4A

PHARMACEUTICAL COMPOSITION FOR TREATING AUTOSOMAL DOMINANT POLYCYSTIC KIDNEY DISEASE

CROSS REFERENCE TO RELATED APPLICATIONS

This application is a continuation of International Application No. PCT/JP2024/046002 filed Dec. 25, 2024, which claims priority to Japan Patent Application No. 2024-194582 filed Nov. 6, 2024, each of which is incorporated by reference herein in its entirety.

TECHNICAL FIELD

This disclosure relates to a new dosage regimen of an oral pharmaceutical composition comprising tamibarotene as an active ingredient for treating and/or preventing autosomal dominant polycystic kidney disease.

BACKGROUND ART

Autosomal dominant polycystic kidney disease (ADPKD) is a difficult-to-treat inherited disorder that progressively forms numerous cysts in the kidneys and progresses to end-stage renal disease after middle age. About 85% of cases are caused by the PKD1 gene and about 15% are caused by the PKD2 gene. Research has been conducted using various experimental animal models such as mice and rats with modified genes; however, a complete understanding of the disease pathology has not been achieved and no radical treatment methods have been developed.

Tolvaptan, a vasopressin V2 receptor antagonist, is the only approved drug for treating ADPKD. It suppresses cyst formation and renal function decline. However, its effects are limited, and it cannot provide a cure. Tolvaptan can cause serious side effects, such as severe liver dysfunction. patients who take tolvaptan are subject to various behavioral restrictions, such as the need for frequent water intake and urination to prevent the development of side effects such as dehydration and hypernatremia due to its strong diuretic effect, so there is a need to develop a novel therapeutic agent that improves patients' quality of life.

In recent years, research has been actively conducted to analyze the detailed pathology and search for therapeutic agents by generating iPS cells from the somatic cells of patients with intractable diseases or disease-specific iPS cells by introducing mutations into the causative genes of iPS cells derived from healthy individuals, and inducing the differentiation of these cells into the affected cell types in vitro, so as to prepare disease models that reproduce the pathology.

To develop a therapeutic agent for the treatment of ADPKD, the inventors created a three-dimensional culture of renal collecting duct tissue that can be used as a renal cyst model in which cysts spontaneously form. The renal cyst model was created by introducing mutations into the PKD1 gene, one of the causative genes of ADPKD, in iPS cells derived from a healthy individual, and then, the iPS cells were differentiated into renal collecting duct tissue by using our unique novel differentiation induction method. Using this disease model, we found that retinoic acid receptor agonists such as TTNPB and AM80 (tamibarotene) suppress cyst formation. We also confirmed that retinoic acid receptor agonists inhibit cyst formation in vivo in an ADPKD model mouse (Patent Document 1: WO 2024/090521).

Tamibarotene, or AM80 (CAS number: 94497-51-5), is approved for the treatment of relapsed and refractory acute promyelocytic leukemia and is marketed as "Amnolake® tablet 2 mg" (non-patent literature 1).

CITATION LIST

Patent Literature

Patent Literature 1: WO2024/090521

Non-Patent Literature

Non-Patent Literature 1: Amnolake® Tablet 2 mg Package Insert (October 2022 Revision, 1st Edition)

SUMMARY OF THE INVENTION

Technical Problem

An object of the present disclosure is to provide a pharmaceutical composition comprising tamibarotene for treating and/or preventing autosomal dominant polycystic kidney disease (ADPKD) in humans. Specifically, this disclosure aims to provide a pharmaceutical composition for the treatment of ADPKD that comprises a specific dosage of tamibarotene.

Solution to Problem

This disclosure provides a pharmaceutical composition for treating or preventing autosomal dominant polycystic kidney disease, comprising tamibarotene as the active ingredient, which is administered orally to a human subject at 1.4 to 5.5 mg/day of tamibarotene.

This disclosure also provides a pharmaceutical composition for treating or preventing autosomal dominant polycystic kidney disease, comprising tamibarotene as the active ingredient, which is administered orally to a human subject at about 4 mg/day of tamibarotene.

BRIEF DESCRIPTION OF DRAWINGS

FIG. 4A Cross-sectional image of cystic kidneys of the tamibarotene administered and unadministered model mice in example 1.

DESCRIPTION OF EMBODIMENTS

Figure 1:
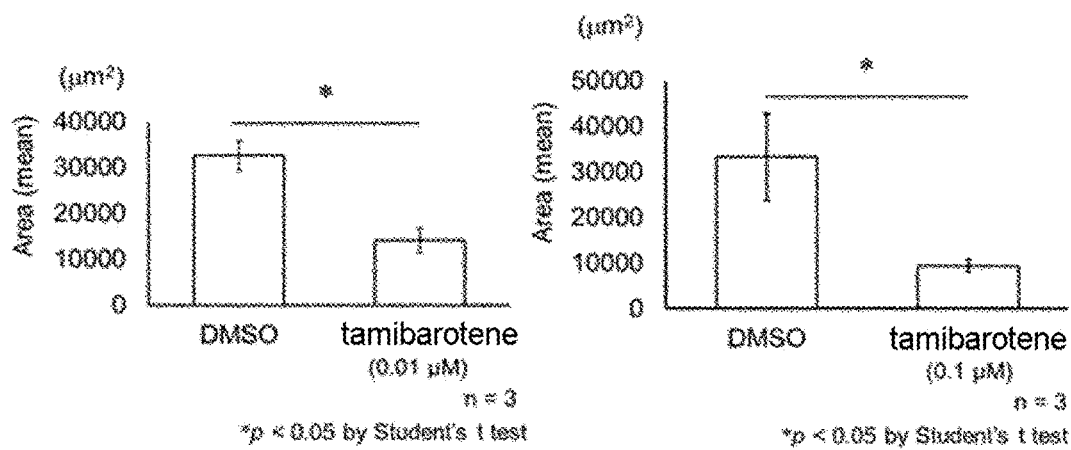
FIG. 1 shows the results of Reference Example 1. Artificial collecting duct organoids with cystic structures were generated from human PKD1 knocked out iPS cell line 1383D2, and used as an in vitro kidney cyst model of ADPKD. The in vitro model was treated with tamibarotene at concentrations of 0.01 UM and 0.1 μM for three days. Suppression of cyst enlargement was observed. The data from three independent experiments are presented as mean±S.D. (n=3). A Student's t-test was performed.

In this disclosure, when a numerical value is accompanied by the term "about", it is intended to include the range of ±10% of that value. For example, "about 20" shall include "18 to 22". The numerical range includes all numerical values between the two endpoints and the numerical values at both endpoints. The term "about" for range applies to both endpoints of that range. For example, "about 20 to 30" shall include "18 to 33".

As used herein, the term "treatment" means, in a subject with a disease, to reduce or eliminate the cause of the disease, to delay or halt the progression of the disease, to reduce, alleviate, ameliorate, or eliminate its symptoms, and/or to inhibit the worsening of its symptoms.

In this disclosure, "prevention" means preventing the onset of a disease in the subject, reducing the likelihood of disease onset, or alleviating or mitigating symptoms in the event that the disease does occur. Here, the onset of the disease includes recurrence after healing or remission. The subject is, for example, one that has a high likelihood of developing the disease but has not yet developed or relapsed. This includes subjects with a genetic predisposition to ADPKD. Genetic mutations in the causative genes of ADPKD, such as PKD1 and PKD2, are mentioned.

The inventors conducted a study on the effective dosage of tamibarotene when administered orally using ADPKD model mice. The inventors obtained pharmacokinetic parameters at the dosage confirmed to be effective in the model mice and calculated the dosage that would yield equivalent pharmacokinetic parameters in humans, thereby determined the expected effective dosage regimen for humans. Based on this dosage regimen, a clinical study was conducted involving patients with ADPKD to confirm the efficacy of the dosage regimen.

Oral administration of tamibarotene at 1.4-5.5 mg/day was identified as effective dosage for humans by our study using the ADPKD model mice. Based on the information, a Phase II clinical study has been conducted with a dosage of tamibarotene at 4.0 mg/day. As a result, some cases in which the subjective symptoms of renal pain were improved with the administration of 4.0 mg/day of tamibarotene have been reported. Additionally, as an interim result of the clinical study, a significant reduction in the rate of increase of total kidney volume (TKV) was observed with the administration of tamibarotene up to 28 weeks.

The pharmaceutical composition comprising tamibarotene provided by this application may include a pharmaceutically acceptable carrier or additive. Examples of such carriers or additives include isotonic agents, thickeners, sugars, sugar alcohols, preservatives, bactericides, antimicrobial agents, pH regulators, stabilizers, chelating agents, oily bases, gel bases, wetting agents, surfactants, suspending agents, binders, excipients, lubricants, disintegrants, foaming agents, fluidizing agents, dispersing agents, emulsifiers, buffering agents, solubilizing aids, and antioxidants. These pharmaceutically acceptable carriers or additives may be used alone or two or more may be used in combination.

The pharmaceutical composition of the present application is administered orally. Examples of dosage forms of the pharmaceutical composition may be granules, fine granules, powders, coated tablets, tablets, suppositories, dispersible powders, capsules, microcapsules, chewable tablets, liquids, suspensions, and emulsions.

A preferred dosage form of the pharmaceutical composition of this application may be a tablet comprising the active ingredient tamibarotene. Examples of excipients and additives for the tablet may include, but not limited to, lactose monohydrate, corn starch, hydroxypropyl cellulose, and magnesium stearate. As a pharmaceutical composition comprising tamibarotene, Amnolake® tablet currently available on the marketed can be used.

The amount of tamibarotene contained in one tablet is not particularly limited. For example, one tablet may contain 1 mg, 2 mg, or 4 mg of tamibarotene.

Tamibarotene is administered orally once daily at a dose of about 4.0 mg. The treatment with tamibarotene may be continued as long as tolerability is not an issue.

Reference Example 1

Artificial collecting duct organoids with cystic structures were induced by the aforementioned method using PKD1 knockout iPS cell strain 1383D2. The effect of tamibarotene to inhibit the cyst enlargement in the renal collecting duct were confirmed by the protocol as follows:

1. Organoids in which cyst formation was occurring were collected in tubes.

2. Medium was removed and 2 ml of Cell Recovery Solution was added. (4° C., 30 minutes)

3. Gel was dissolved by gentle pipetting with a P-1000 pipetteman and then centrifuged. (500 g, 2 minutes)

4. After removing the supernatant from 3 and adding 5 ml of FBS-containing medium (STO medium), cysts were separated from the organoids by pipetting.

5. Using a stereomicroscope, cysts were collected in 15 ml tubes.

6. The supernatant was removed, and then 2 ml of Accutase was added to perform treatment at 37° C. for 5 minutes.

7. Cells were dissociated down to single cells by pipetting with a P-1000 Pipetteman®.

8. After filtering, number of the cells was counted.

9. After cell counting, a cell suspension containing the required number of the cells was transferred to a tube, and then 5 ml of FBS-containing medium (STO medium) was added to stop the Accutase reaction. To seed at $5\times10^4$ cells/well, the amount of the cell suspension required was calculated.

10. Pellets were prepared by centrifugation (200 g, 5 minutes).

11. The supernatant was thoroughly removed, and then DMEM/F12+B27 w/o V.A. medium (10% Afamin/Wnt3a CM, 200 ng/ml R-Spondin 1, 200 ng/ml FGF1, 10 µM Forskolin, 2.5 µM AVP, 10 µM Y27632) was added for suspension. To seed at $5\times10^4$ cells/well, the amount of required medium was calculated.

12. The cell suspension from 11 was seeded at $5 \times 10^4$ cells/well into pre-prepared 50% Matrigel plates. The cell suspension was added slowly to avoid disrupting the Matrigel.

13. Cyst structures were prepared by culturing cells at 37° C. with 5% $CO_2$ for 2 days.

14. The medium was removed, DMEM/F12+B27 w/o V.A. medium comprising 200 ng/ml FGF1, 2.5 µM AVP and 0.01 µM or 0.1 µM tamibarotene was added, then, cultured for 3 days at 37° C. with 5% $CO_2$. DMSO was used in the control group.

15. Nine (9) locations inside the wells were photographed using a 4× objective lens under a fluorescence microscope (Keyence, BZ-X700), the cyst area was measured using a BZ-X Analyzer, and then the average value was calculated. The results are shown in FIG. 1.

Inhibition of cyst enlargement was observed at both tamibarotene concentrations, 0.01 µM and 0.1 µM.

Example 1

Creation of ADPKD Model Mice

The Pkd1$^{flox/flox}$ mice established by Shibazaki et al. (Shibazaki S., Hum Mol Genet. 2008, 1505-1516) were crossed with the Mx1-Cre mice (The Jackson Laboratory, Maine, USA) to produce the Pkd1$^{flox/+}$: Mx1-Cre mice. The Pkd1$^{flox/+}$: Mx1-Cre mice were then crossed with the Pkd1$^{flox/flox}$ mice to produce the Pkd1$^{flox/flox}$: Mx1-Cre mice. The Pkd1$^{flox/flox}$: Mx1-Cre mice can delete Pkd1 at any time by expressing the Cre gene under the control of the interferon-responsive Mx1 gene promoter. (Cre-loxP site-specific recombination). The expression of the Cre gene is induced by polyinosinic-polycytidylic acid (pI-pC) which stimulates the production of interferon.

An adult-onset ADPKD model mouse was created by continuously administering 10 µg/g (BW) of pI-pC intraperitoneally to the Pkd1$^{flox/flox}$: Mx1-Cre mouse for 6 days beginning on postnatal day 10, to induce Pkd1 deletion.

The tamibarotene solution was prepared by first diluting the tamibarotene in 100% dimethyl sulfoxide (DMSO), and then diluting it 250 times with methylcellulose. The solution was administered orally once daily to adult-onset ADPKD model mice at doses of 0.2 mg/kg or 1.0 mg/kg, starting at postnatal day 28. As a control, 0.4% DMSO in methylcellulose was administered.

Urine samples were collected via 24-hour urine collection on 22 days after the start of administration (on postnatal day 50). On 28 days after the start of administration (on postnatal day 56), body weight was measured and all animals were sacrificed. The kidneys and livers were removed and weighed.

Measurement of Urea Nitrogen (UN)

UN was measured using the UN-L kit (A666-00, Serotec Co., Ltd.).

Hematoxylin-Eosin (HE) Staining and Measurement of the Cystic Index

The kidneys and livers were fixed in 4% paraformaldehyde solution, and 4 µm-thick paraffin embedded sections were prepared. The sections were dewaxed and stained with HE. The images of the renal tissues were photographed under an optical microscope. Cystic index was calculated by using image analysis and measurement software (Win-ROOF, Mitani Corporation):

total cystic area/total renal tissue area×100 or total cystic area/total liver area×100.

Statistical analysis was conducted using the maximum contrast method. The results are shown in FIGS. 2 to 5B.

Figure 2:
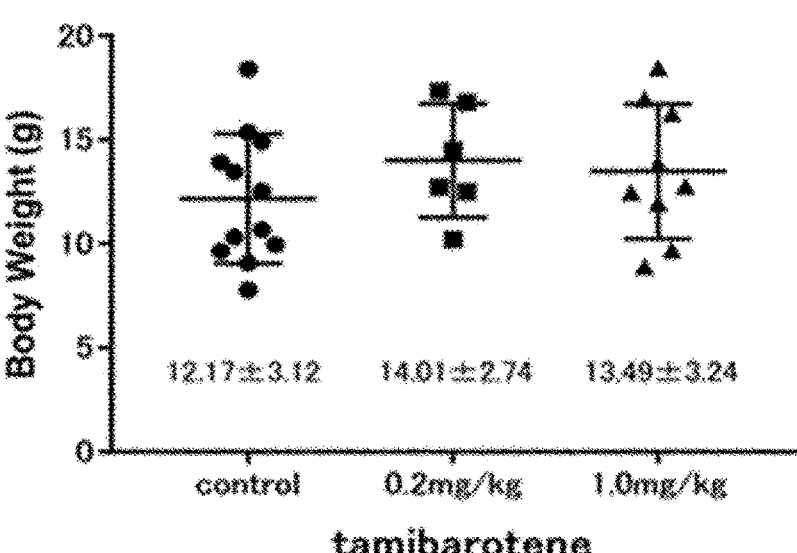
FIG. 2 The results of Example 1 are shown. Tamibarotene was administered orally to the adult-onset ADPKD model mice once daily for 28 days at doses of 0.2 mg/kg and 1.0 mg/kg. The figure illustrates the difference in body weight between tamibarotene-administered and unadministered groups.
Figure 3:
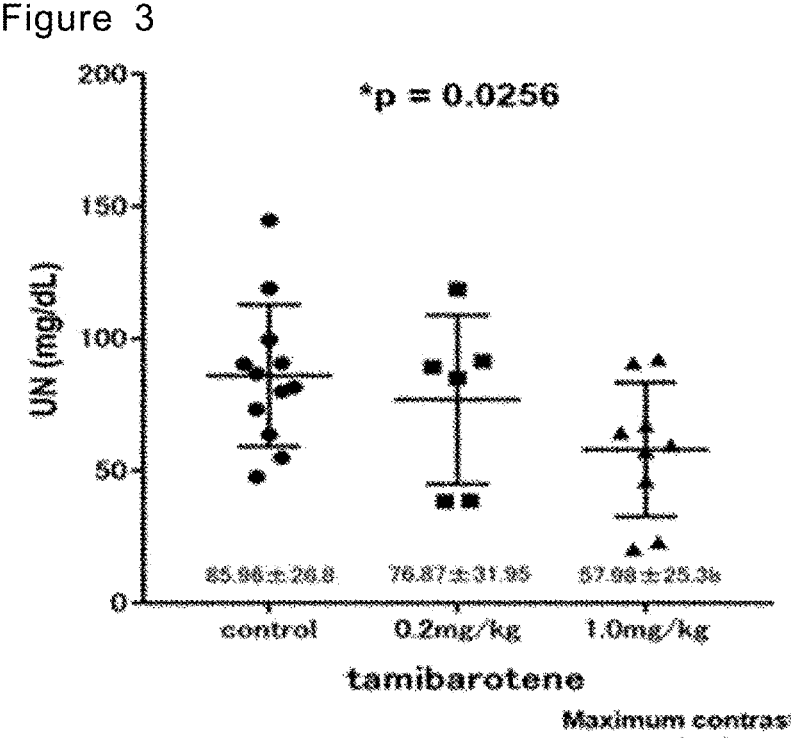
FIG. 3 shows the difference in Urea Nitrogen (UN) between mice of the tamibarotene-administered and unadministered groups.
Figure 4A:
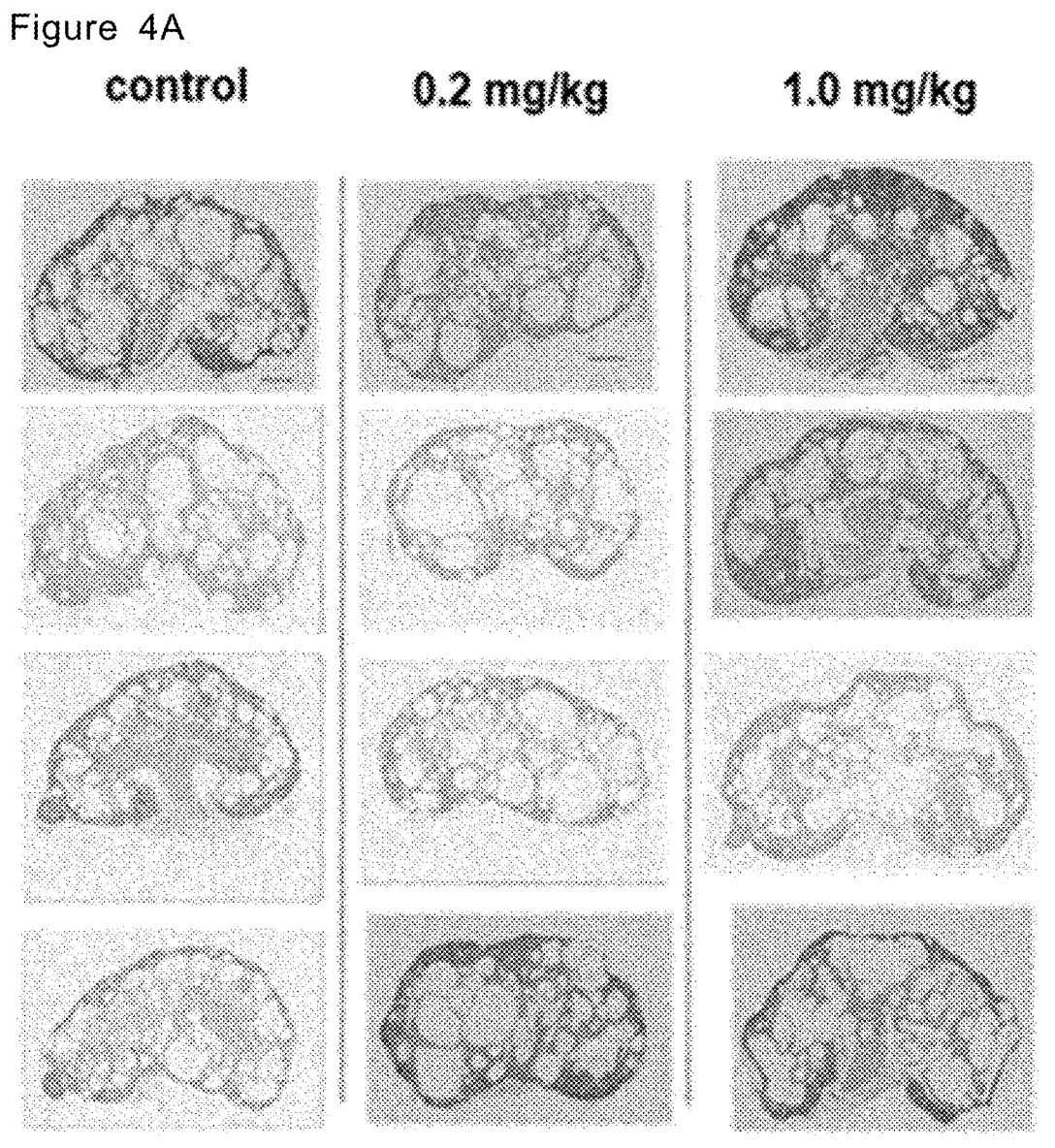
Figure 4B:
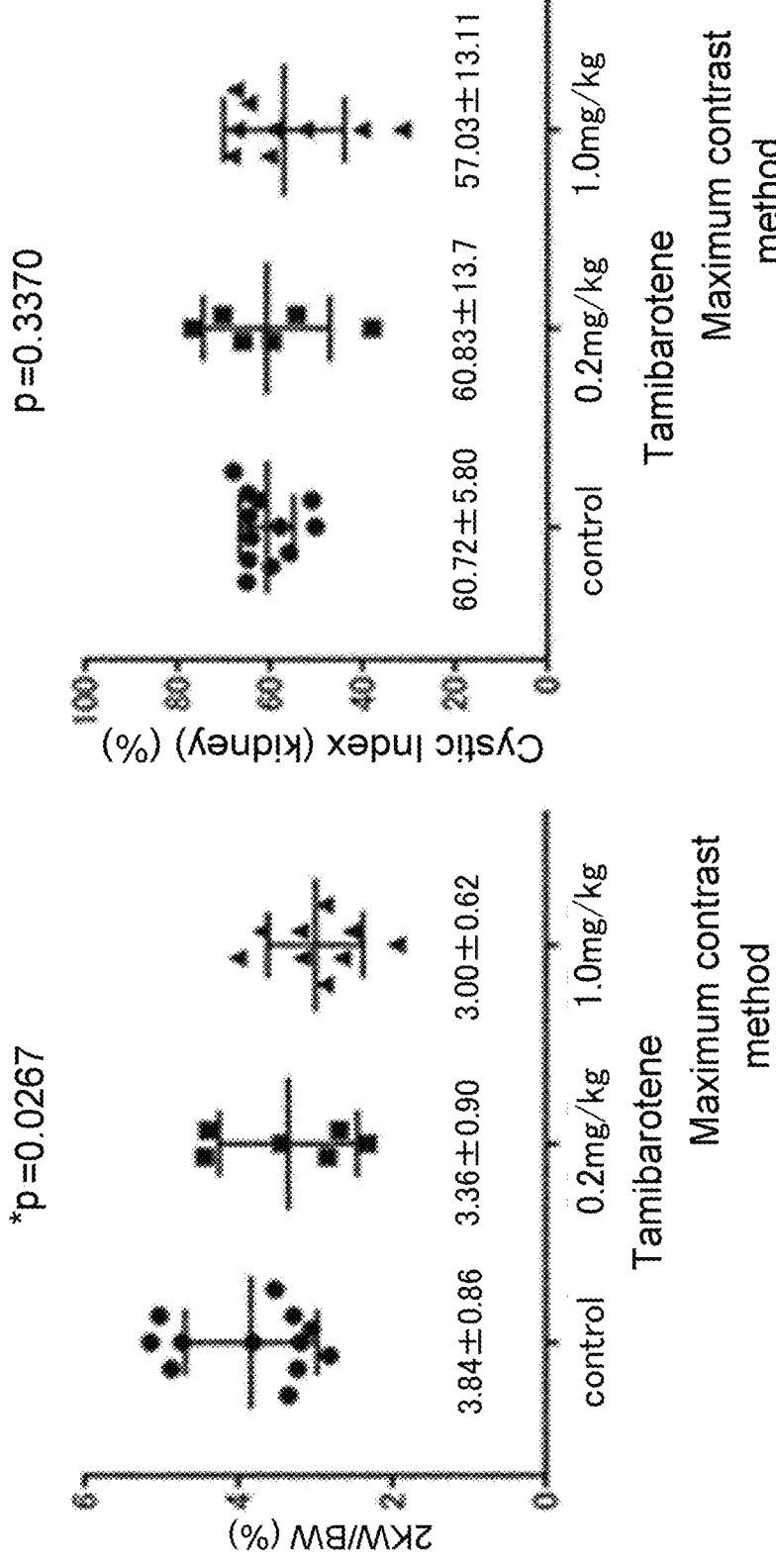
FIG. 4B The kidney weight-to-body weight ratio (2 KW/BW) and the kidney cystic index of the tamibarotene administered and unadministered model mice in example 1.
Figure 5A:
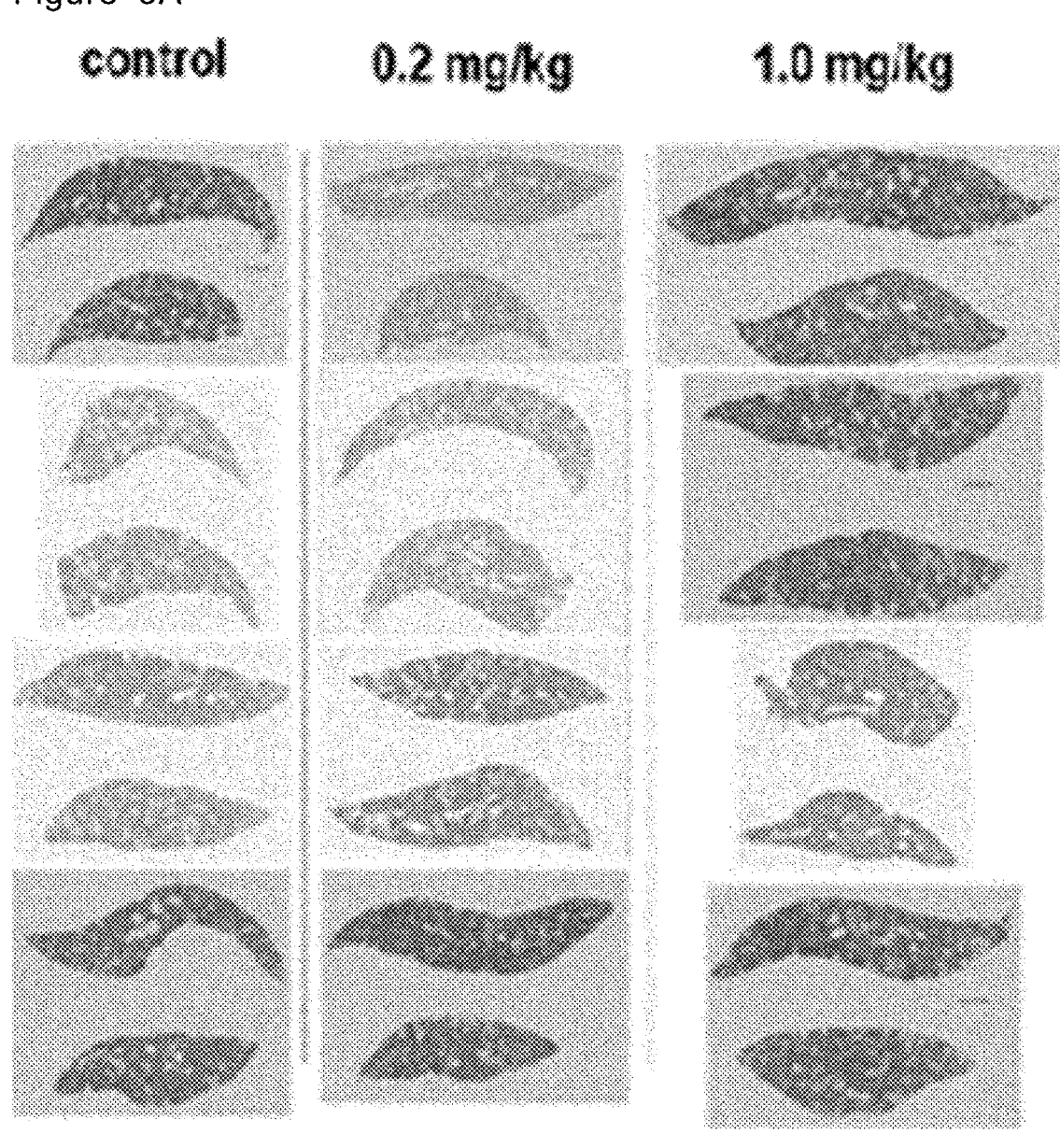
FIG. 5A Cross-sectional view of the liver of the tamibarotene administered and unadministered model mice in example 1.
Figure 5B:
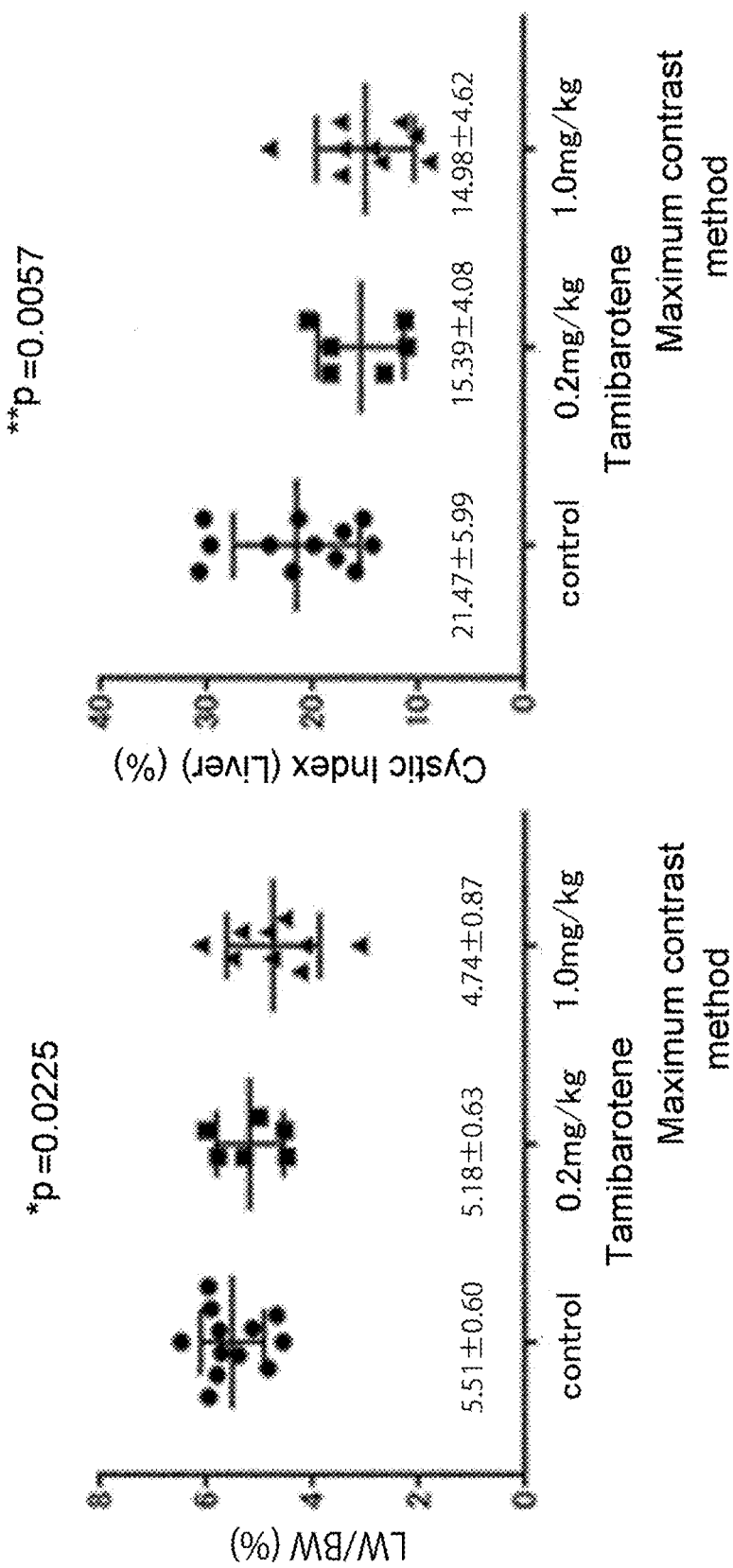
FIG. 5B Changes in the liver weight-to-body weight ratio (LW/BW) and liver cystic index of the tamibarotene administered and unadministered model mice in example 1.

There was no difference in body weight between the control (solvent only) group and the tamibarotene group (FIG. 2). The Urea Nitrogen (UN) and kidney weight-to-body weight ratio (2 KW/BW) significantly decreased in the tamibarotene group (FIGS. 3, 4A and 4B). The cystic index of the kidney did not show any difference by tamibarotene (FIGS. 4A and 4B), but both the liver weight-to-body weight ratio (LW/BW) and the cystic index of the liver significantly decreased in the tamibarotene group (FIGS. 5A and 5B).

From the results of Example 1, it was confirmed that the dosages of 0.2 and 1.0 mg/kg/day in the ADPKD model mice are effective for the suppression of cyst formation.

Example 2

Pharmacokinetics in Mice

Figure 6:
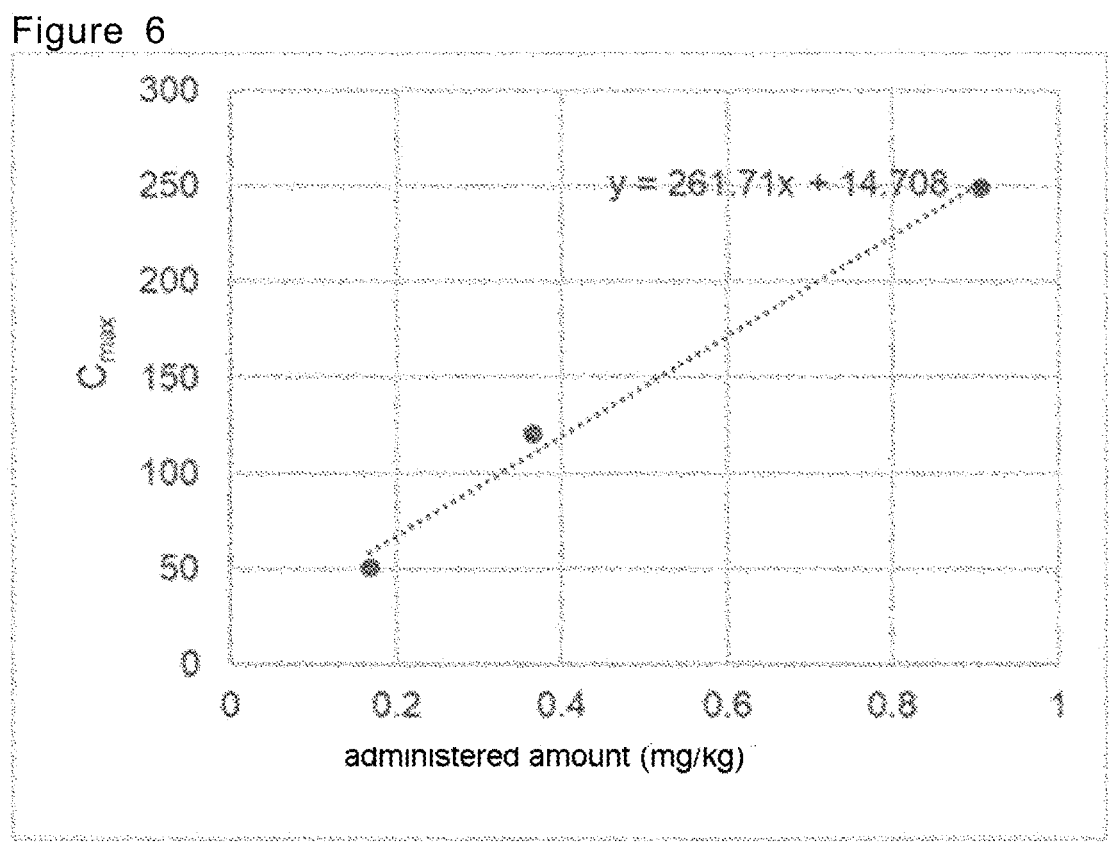
FIG. 6 Correlation between the amount of the administered tamibarotene and the Cmax.
Figure 7:
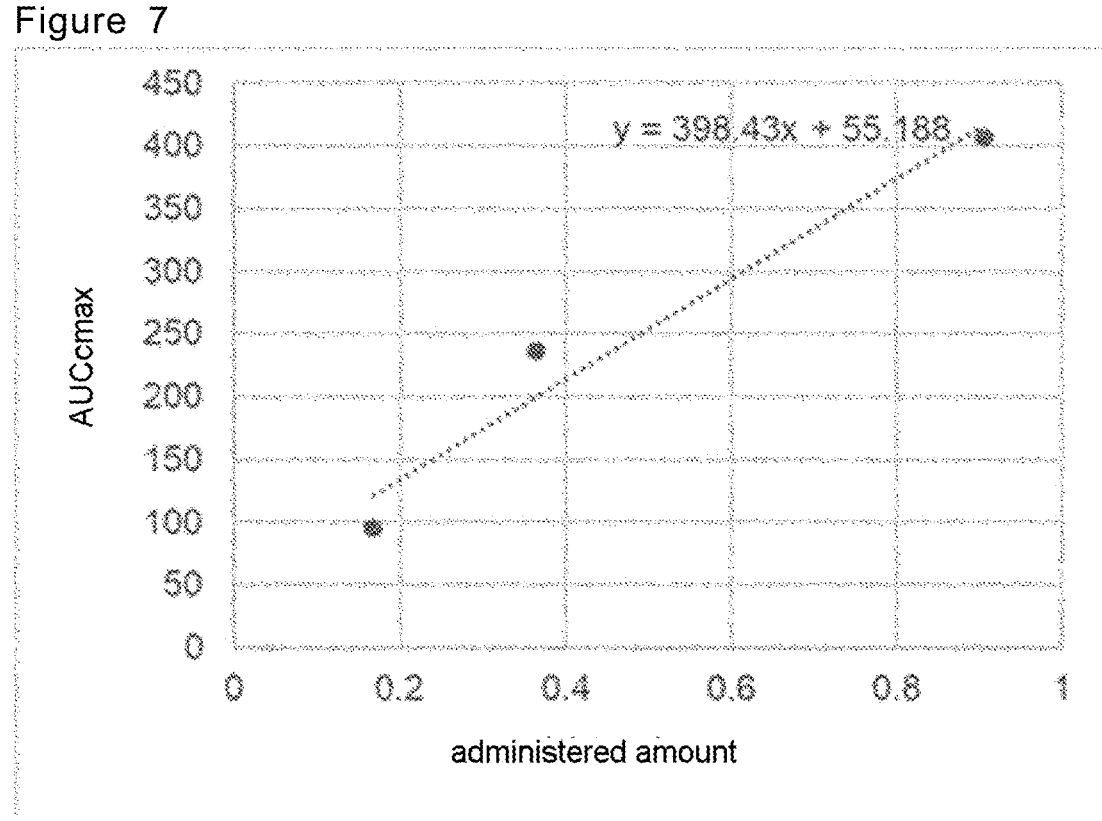
FIG. 7 Correlation between the amount of the administered tamibarotene and the $AUC_{0-inf}$ in mice.

The pharmacokinetics of tamibarotene administered orally were measured using C57BL/6J mice. Table 1 and FIG. 6 illustrate the pharmacokinetic parameters of tamibarotene administered orally in mice. FIG. 7 illustrates the correlation between tamibarotene dose and $AUC_{0\text{-}inf}$.

In Example 1, the cyst formation inhibitory effect was confirmed at a dose of 0.2 mg/kg tamibarotene in ADPKD model mice. The Cmax at that dose was about 67 ng/mL, which was about 20 times higher than the concentration of 0.01 µM (3.5 ng/mL) which was confirmed to inhibit cyst enlargement in the in vitro renal cyst model.

TABLE 1

| Dose (mg/kg) | Cmax (ng/mL) | Tmax (h) | T½ (h) | $AUC_{0\text{-}inf}$ (ng h/mL) |
|---|---|---|---|---|
| 0.167 | 50.9 ± 14.7 | 0.5 | 1.84 ± 0.59 | 95.1 ± 24.8 |
| 0.365 | 120.5 ± 37.1 | 0.5 | 1.94 ± 0.47 | 236.5 ± 30.9 |
| 0.905 | 248.8 ± 89.6 | 0.5 | 2.11 ± 1.40 | 406.0 ± 95.2 |

Calculation of Human Dosage

Dosages of 0.2 and 1.0 mg/day were confirmed to effectively suppress cyst formation in the ADPKD model mice. Based on the $AUC_{0\text{-}inf}$ in Table 1 and FIG. 7, as well as the $AUC_{0\text{-}inf}$ in APL patients (128.37 ng·h/mL for 2.0 mg/day, 320.41 ng·h/mL for 4.0 mg/day, and 430.26 ng·h/mL for 6.0 mg/day of tamibarotene, according to the Amnolake® 2 mg tablet interview form), the human dosage corresponding to the dosage effective in mice was calculated. The dosage expected to be effective in a clinical study in humans was determined to be between 1.4 and 5.5 mg/body (Table 2).

TABLE 2

| | Dose in Mice | | |
|---|---|---|---|
| | 0.167 mg /kg | 0.365 mg/kg | 0.905 mg/kg |
| $AUC_{0\text{-}inf}$ | 95.1 ng h/mL | 236.5 ng h/mL | 406.0 ng h/mL |
| Corresponding Dose in Humans | 1.4 mg/body | 3.3 mg/body | 5.5 mg/body |

Example 3

Pharmacokinetics of Tamibarotene in Human Patients with ADPKD

The pharmacokinetics of the drug in patients with ADPKD were examined in the early Phase II clinical study of tamibarotene.

In seven patients with ADPKD, the average $AUC_{0-inf}$ after a single 4 mg/body administration of tamibarotene was 282.1 ng h/mL, and the average $AUC_{0-inf}$ after 7 days of daily administration was 270.6 ng h/mL. These values were then converted to mice, confirming corresponding values of 0.57 mg/body and 0.54 mg/body, respectively (Table 3).

Accordingly, the human dose corresponding to the mouse dose of 0.365 to 0.905 mg/kg in Table 2 of Example 2 is about 3.3 to 5.5 mg/body, confirming that the clinical dosage predicted from the pharmacokinetic results of tamibarotene in patients with APL is reasonable for patients with ADPKD.

TABLE 3

|  | Dosage in ADPKD patients | |
| --- | --- | --- |
|  | 4 mg/body single | 4 mg/body 7 days of daily |
| $AUC_{0-inf}$ | 282.1 ng h/mL | 270.6 ng h/mL |
| Corresponding dosage in mice | 0.57 mg/body | 0.54 mg/body |

Example 4

Phase II Clinical Study
    Purpose: To evaluate the efficacy, safety, and pharmacokinetics of tamibarotene in patients with autosomal dominant polycystic kidney disease (ADPKD)
Inclusion Criteria:
    Phase II clinical study was conducted on patients diagnosed with ADPKD according to the modified Pei-Ravine criteria shown below:
Mayo Classification: Class 1C, 1D or 1E Chronic Kidney Disease Epidemiology
    Collaboration (CKD-EPI) cr-cys (eGFR) is equal to or greater than 60 mL/min/1.73 m²
    Patients who are judged to be hard to treat with tolvaptan or who do not wish to be treated with tolvaptan, at the time of obtaining consent
    Patients with systolic blood pressure below 140 mmHg and diastolic blood pressure below 90 mmHg.
    For patients receiving angiotensin-converting enzyme inhibitors or angiotensin II receptor antagonists, the dose must be constant for at least 6 weeks before obtaining informed consent
Exclusion Criteria:
    Women who are pregnant or may be pregnant
    Nursing mother
    Females with childbearing potential or male subjects with a fertile partner who is unable to use contraception for the following periods:
    1. Female: From informed consent to 2 years after the last administration of the study drug
    2. Male: From informed consent to 6 months after the last administration of the study drug
    Patients within 12 weeks from the last dose of a drug that affects renal cysts, such as tolvaptan, immune suppressor, somatostatin analogs, Sodium Glucose Cotransporter 2 (SGLT2) inhibitors, biguanide antidiabetic drugs, and pioglitazone-containing formulations with a period of 12 weeks or less from the last administration date to the first administration date of the study drug.
    Patients with complications of intracranial aneurysms that require treatment.

Patients with complications of malignant tumor.
    Patients with complications of uncontrolled diabetes who have 7.0% or higher hemoglobin Alc (HbAlc) despite treatment.
    Patients with lumbar spine bone density <70% determined by dual-energy X-ray absorptiometry (DEXA) or with fragility fractures in any part of the body.
    Patients with complications of uncontrolled dyslipidemia who have low-density lipoprotein (LDL) cholesterol of 160 mg/dL or higher or triglycerides (TG) of 175 mg/dL or higher despite treatment.
    Patients with aspartate aminotransferase (AST) or alanine aminotransferase (ALT) levels above the upper reference limit.
Usage and Dosage
    Tamibarotene 4.0 mg (tablet) or the placebo tablet was orally administered once daily for 52 weeks.
Confirmation of the Effect
    CT images of the kidney region of the test subjects were obtained at the time of obtaining the informed consent for participation in the clinical study, at the start of the administration of tamibarotene, and 28 weeks after the start of the administration. The period from obtaining the informed consent to the start of the administration was within one year. Using the image analysis software "SYNAPSE VINCENT" (Fujifilm Corporation), the total kidney volume (TKV) was obtained from the CT image data by a radiological diagnostic specialist in accordance with standard practices.
Interim Results of the Clinical Study
    Changes (slope) in total kidney volume (TKV) in patients (7 cases) who received oral administration of tamibarotene 4.0 mg (tablet) once daily for 28 weeks (6 months) are illustrated in Table 4 and FIG. 8.

TABLE 4

| Slope | From informed consent to the 1st administration | From the 1st administration to 28 weeks of administration |
| --- | --- | --- |
| PK1 | 0.152 | 0.021 |
| PK2 | 0.003 | 0.009 |
| PK3 | 0.200 | 0.172 |
| PK4 | 0.117 | 0.127 |
| PK5 | 0.151 | 0.035 |
| PK6 | 0.222 | 0.011 |
| PK7 | 0.234 | 0.144 |
| Average | 0.154 | 0.074 |
| SD | 0.079 | 0.070 |

Figure 8:
FIG. 8 shows the results of a clinical study in which tamibarotene was administered at a dose of 4 mg/day to patients with autosomal dominant polycystic kidney disease, up to the 28th week after the start of the study.
Figure 8:
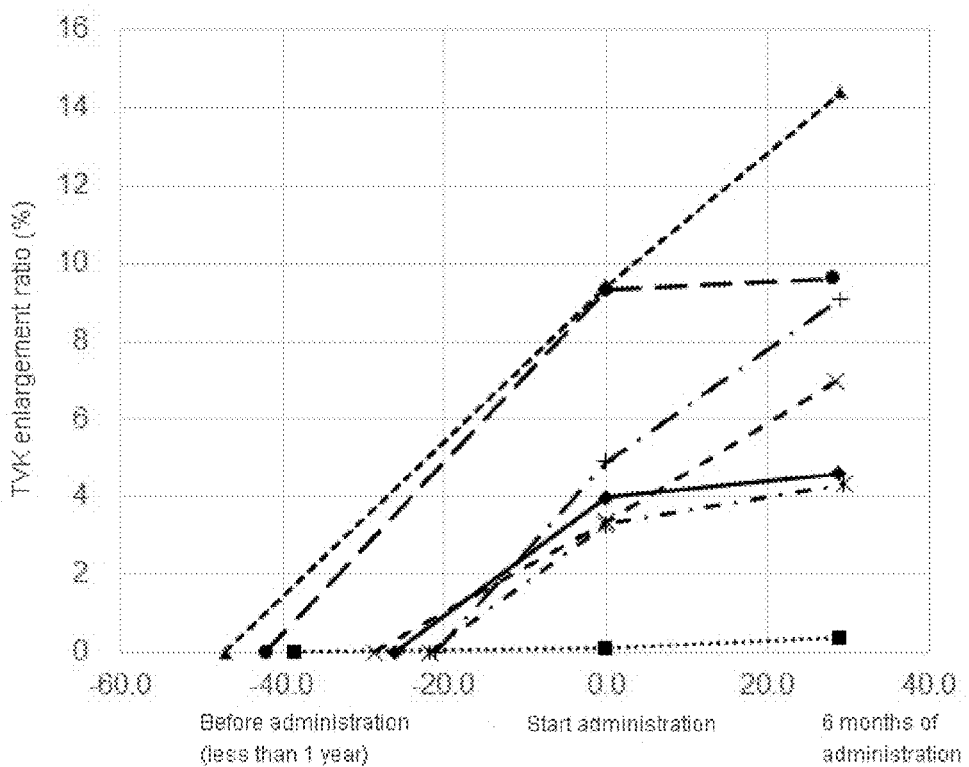

As illustrated in FIG. 8, in 5 out of 7 cases, it was confirmed that the administration of tamibarotene significantly reduced the rate of increase in the Total Kidney Volume (TKV).

The invention claimed is:
    1. A method for treating autosomal dominant polycystic kidney disease (ADPKD) in a subject in need thereof, the method comprising administering 1.4-5.5 mg/day of tamibarotene orally to the subject.
    2. A method for treating autosomal dominant polycystic kidney disease (ADPKD) in a subject in need thereof, the method comprising administering about 4 mg/day of tamibarotene orally to the subject.

* * * * *